(12) United States Patent
Guichard et al.

(10) Patent No.: US 11,179,713 B2
(45) Date of Patent: Nov. 23, 2021

(54) PROCESS FOR THE PREPARATION OF A CATALYST WHICH CAN BE USED IN HYDROTREATMENT AND HYDROCONVERSION

(71) Applicants: TOTAL RAFFINAGE MARKETING, La Defense (FR); IFP Energies nouvelles, Rueil-Malmaison (FR)

(72) Inventors: Bertrand Guichard, Izeaux (FR); Laurent Simon, Villeurbanne (FR); Sylvie Lopez, Lyons (FR); Valentina De Grandi, Schaerbeek (BE); Delphine Minoux, Nivelles (BE); Jean-Pierre Dath, Beloeil (BE)

(73) Assignees: IFP ENERGIES NOUVELLES, Rueil-Malmaison (FR); TOTAL RAFFINAGE MARKETING, La Defense (FR)

( * ) Notice: Subject to any disclaimer, the term of this patent is extended or adjusted under 35 U.S.C. 154(b) by 241 days.

(21) Appl. No.: 13/720,026

(22) Filed: Dec. 19, 2012

(65) Prior Publication Data

US 2013/0165316 A1 Jun. 27, 2013

(30) Foreign Application Priority Data

Dec. 22, 2011 (FR) ...................................... 1104026

(51) Int. Cl.
*B01J 27/051* (2006.01)
*B01J 37/02* (2006.01)
(Continued)

(52) U.S. Cl.
CPC ........... *B01J 37/0205* (2013.01); *B01J 23/24* (2013.01); *B01J 23/28* (2013.01); *B01J 23/85* (2013.01);
(Continued)

(58) Field of Classification Search
CPC ... B01J 31/34; B01J 37/12; B01J 37/28; B01J 37/0203; B01J 23/28; B01J 23/75;
(Continued)

(56) References Cited

U.S. PATENT DOCUMENTS 7,956,000 B2 6/2011 Jansen et al.
8,128,811 B2 3/2012 McCarthy et al.
(Continued)

FOREIGN PATENT DOCUMENTS

EP 1900430 A1 3/2008
WO 2005035691 A1 4/2005
(Continued)

OTHER PUBLICATIONS

Search Report related to FR1104026 dated Jul. 12, 2012.

*Primary Examiner* — Jun Li
(74) *Attorney, Agent, or Firm* — Millen White Zelano and Branigan, PC; John Sopp

(57) ABSTRACT

A process for the preparation of a catalyst from a catalytic precursor comprising a support based on alumina and/or silica-alumina and/or zeolite and comprising at least one element of group VIB and optionally at least one element of group VIII, by impregnation of said precursor with a solution of a C1-C4 dialkyl succinate. An impregnation step for impregnation of said precursor which is dried, calcined or regenerated, with at least one solution containing at least one carboxylic acid other than acetic acid, then maturing and drying at a temperature less than or equal to 200° C., optionally a heat treatment at a temperature lower than 350° C., followed by an impregnation step with a solution containing at least one C1-C4 dialkyl succinate followed by maturing and drying at a temperature less than 200° C. without subsequent calcination step. The catalyst is used in hydrotreatment and/or hydroconversion.

41 Claims, 1 Drawing Sheet

(51) Int. Cl.
| | |
|---|---|
| *B01J 37/20* | (2006.01) |
| *B01J 23/28* | (2006.01) |
| *B01J 27/14* | (2006.01) |
| *B01J 38/52* | (2006.01) |
| *B01J 37/28* | (2006.01) |
| *C10G 45/08* | (2006.01) |
| *B01J 23/882* | (2006.01) |
| *C07C 5/10* | (2006.01) |
| *B01J 38/62* | (2006.01) |
| *B01J 23/90* | (2006.01) |
| *B01J 27/19* | (2006.01) |
| *B01J 23/85* | (2006.01) |
| *B01J 31/02* | (2006.01) |
| *B01J 35/00* | (2006.01) |
| *C10G 45/50* | (2006.01) |
| *B01J 23/24* | (2006.01) |
| *B01J 21/04* | (2006.01) |
| *B01J 29/076* | (2006.01) |

(52) U.S. Cl.
CPC ............ *B01J 23/882* (2013.01); *B01J 23/90* (2013.01); *B01J 27/051* (2013.01); *B01J 27/14* (2013.01); *B01J 27/19* (2013.01); *B01J 31/0201* (2013.01); *B01J 31/0209* (2013.01); *B01J 35/002* (2013.01); *B01J 37/0203* (2013.01); *B01J 37/20* (2013.01); *B01J 37/28* (2013.01); *B01J 38/52* (2013.01); *B01J 38/62* (2013.01); *C07C 5/10* (2013.01); *C10G 45/08* (2013.01); *C10G 45/50* (2013.01); *B01J 21/04* (2013.01); *B01J 29/076* (2013.01); *C07C 2601/14* (2017.05); *Y02P 20/584* (2015.11)

(58) Field of Classification Search
CPC . B01J 23/882; B01J 23/85; B01J 38/52; B01J 38/62; B01J 29/90; B01J 37/0205; B01J 37/20; B01J 27/051; C01G 45/08; C01G 45/12; C07C 5/10
USPC .................... 502/150; 208/111.3, 111.35
See application file for complete search history.

(56) References Cited

U.S. PATENT DOCUMENTS

| | | | |
|---|---|---|---|
| 8,334,231 | B2 | 12/2012 | Mao et al. |
| 9,079,174 | B2 * | 7/2015 | Simon .................... B01J 29/166 |
| 9,174,202 | B2 * | 11/2015 | Marchand ................ B01J 23/28 |
| 2007/0275845 | A1 | 11/2007 | Jansen et al. |
| 2008/0146438 | A1 * | 6/2008 | Bai et al. ...................... 502/173 |
| 2008/0194892 | A1 | 8/2008 | Cholley et al. |
| 2009/0258779 | A1 * | 10/2009 | McCarthy et al. ............. 502/24 |
| 2009/0261019 | A1 | 10/2009 | McCarthy et al. |
| 2010/0032341 | A1 | 2/2010 | Mao et al. |
| 2011/0094939 | A1 | 4/2011 | Jansen et al. |
| 2013/0008829 | A1 | 1/2013 | Marchand et al. |

FOREIGN PATENT DOCUMENTS

| | | |
|---|---|---|
| WO | 2006077326 A1 | 7/2006 |
| WO | 2009126319 A1 | 10/2009 |
| WO | 2011080407 A1 | 7/2011 |

* cited by examiner

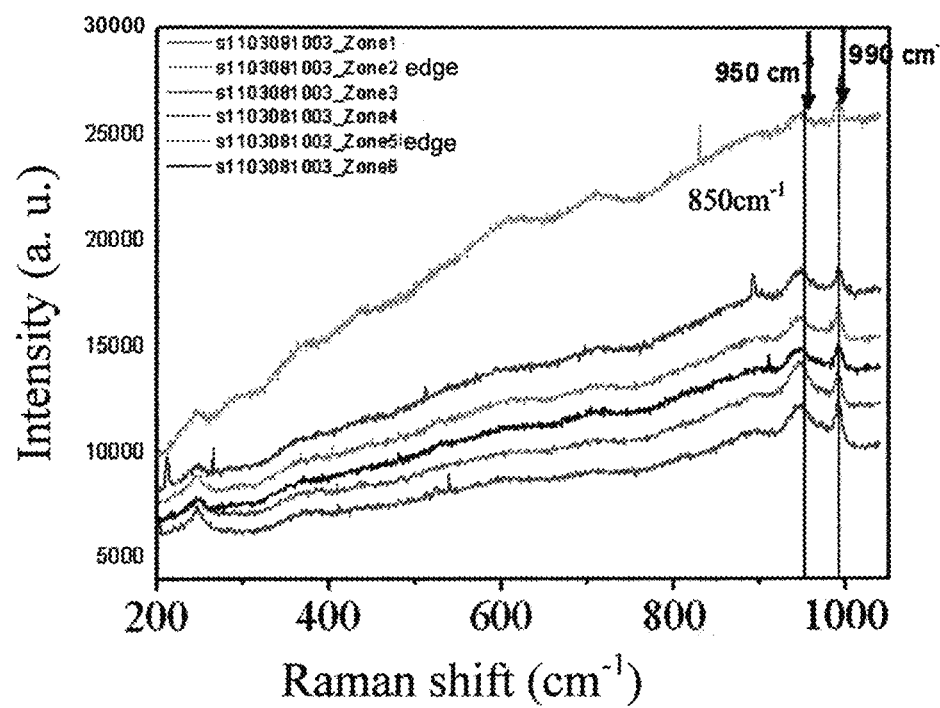

PROCESS FOR THE PREPARATION OF A CATALYST WHICH CAN BE USED IN HYDROTREATMENT AND HYDROCONVERSION

The invention concerns a process for the preparation of a catalyst comprising a support and a hydro-dehydrogenating function, said process comprising the introduction of an additive which is a C1-C4 dialkyl succinate.

PRIOR ART

The use of additive to improve the activity of a dried, calcined or regenerated catalyst is well known to the man skilled in the art. EP0870003 thus teaches that the use of compounds having at least 2 hydroxyl functions or corresponding polyethers introduced in the presence of solvent (alcohols or water) by impregnation of a calcined or regenerated catalytic precursor leads to a gain in activity on condition of preserving at least 50% of the additive and preferably 70% on the catalyst after the final heat treatment. That preparation protocol does not concern the use of carboxylic acid.

WO2006/077326 proposes the use of a catalyst comprising metals of groups VIB and VIII, a refractory oxide as a support, and an organic compound comprising at least 2 carboxylic ester functions of the formula R1-O—CO—R2-CO—O—R1 or R1-CO—O—R2-O—CO—R1 in which each R1 independently represents a C1 to C18 alkyl group, C2 to C18 alkenyl group, C6 to C18 aryl group, C3 to C8 cycloalkyl group, C7 to C20 alkylaryl or arylalkyl group, or the 2 groups R1 jointly form a C2 to C18 divalent group, and R2 represents a C1 to C18 alkylene group, a C6 to C18 arylene group or a C3 to C7 cycloalkylene group, or a combination thereof, wherein the carbonaceous chain of the hydrocarbon groups represented by R1 and R2 may contain or carry one or more heteroatoms selected from N, S and O, and each of the groups R1 and R2 can carry one or more substituents of the formula —C(=O)O—R1 ou —O—C(=O)—R1 in which R1 is of the above-indicated meaning. A preferred mode uses C1-C4 dialkyl succinate and in particular dimethyl succinate given by way of example. Those compounds can be introduced in the presence of a solvent (a significant list of solvents is quoted among which carboxylic acids appear).

Patent application WO11/080,407 describes the simultaneous incorporation of a C1-C4 dialkyl succinate in the presence of acetic acid. The combination of the two compounds makes it possible to considerably enhance the catalytic performances on dried catalysts. WO05/035691 claims an activation process making it possible to reduce the proportion of crystallised phase of type $CoMoO_4$ present on regenerated catalysts comprising oxides of metals of groups VIII and VIB. This process describes contacting a regenerated catalyst with an acid and an organic additive. Simultaneous impregnation of the combination of citric acid (CA) and polyethylene glycol (PEG) has been set forth by way of example on a regenerated catalyst. The examples show the attraction of a citric acid/PEG pair.

Carboxylic acids are described in EP0482817 for the preparation of dried catalysts having a high level of activity, that is to say not calcined, and without any other addition of organic molecules.

DESCRIPTION OF THE INVENTION

The present invention concerns a process for the preparation of a catalyst and its use for hydrotreatment and hydroconversion. An improvement in catalytic performances (in particular catalytic activity) is achieved in relation to the catalysts in the prior art. In fact it has been demonstrated that the use of a particular preparation method, using at least C1-C4 dialkyl succinate and in particular dimethyl succinate, and at least one carboxylic acid other than acetic acid, in the presence optionally of acetic acid, on a dried, calcined or regenerated catalytic precursor, surprisingly leads to markedly improved catalytic activity.

The catalyst has a Raman spectrum with bands at 990 and/or 974 $cm^{-1}$ characteristic of at least one Keggin heteropolyanion and optionally bands characteristic of said succinate. The lines corresponding to the succinate are or are not present accordingly to the conditions of the process, in particular the conditions of the drying operations.

The invention also concerns the activated catalyst and its use in a hydrotreatment and/or hydroconversion process. The activated catalyst is obtained by sulphuration of the catalyst described in the present application.

The catalyst comprises a support and a hydro-dehydrogenating function and phosphorus. The hydro-dehydrogenating function comprises at least one element from group VIB (preferably molybdenum and/or tungsten) and optionally (and preferably) at least one element from group VIII (preferably cobalt and/or nickel). Preferably the hydro-dehydrogenating function comprises molybdenum and cobalt and/or nickel.

The catalyst obtained has a characteristic Raman spectrum grouping together:
1) bands characteristic of the heteropolyanion or heteropolyanions of type Keggin $PXY_{11}O_{40}^{x-}$ and/or $PY_{12}O_{40}^{x-}$ in which Y is a metal of group VIB and X is a metal of group VIII.

According to Griboval, Blanchard, Payen, Fournier and Dubois in Catalysis Today 45 (1998) 277 FIG. 3 e) the main bands of the structure $PCoMo_{11}O_{40}^{x-}$ are on a dried catalyst at 232, 366, 943, 974 $cm^{-1}$ and according to M. T. Pope "Heteropoly and Isopoly oxometalates", Springer Verlag, p 8, those bands are not characteristic of the nature of the atom X or Y but in fact of the structure of the heteropolyanion. The most intense characteristic band of this type of lacunary Keggin heteropolyanion occurs at 974 $cm^{-1}$.

According to Griboval, Blanchard, Gengembre, Payen, Fournier, Dubois and Bernard, Journal of Catalysis 188 (1999) 102, FIG. 1 a), the main bands of $PMo_{12}O_{40}^{x-}$ are in the mass state of the heteropolyanion, for example with cobalt as a counter-ion at 251, 603, 902, 970, 990 $cm^{-1}$. The most intense characteristic band of that Keggin heteropolyanion occurs at 990 $cm^{-1}$. M. T. Pope "Heteropoly and Isopoly oxometalates", Springer Verlag, p 8, also teaches us that those bands are not characteristic of the nature of the atom X or Y, but indeed of the structure of complete, lacunary or substituted Keggin heteropolyanion.

2) Optionally characteristic bands of the dialkyl succinate or succinates used. The Raman spectrum of dimethyl succinate constitutes an unequivocal imprint of that molecule. In the spectral range 300-1800 $cm^{-1}$ that spectrum is characterised by the series of following bands (only the most intense bands are specified in $cm^{-1}$): 391, 853 (the most intense band), 924, 964 and 1739 $cm^{-1}$. The most intense band characteristic of dimethyl succinate is 853 $cm^{-1}$. The spectrum of diethyl succinate comprises the following main bands in the spectral range considered: 861 (most intense band), 1101 and 1117 $cm^{-1}$. Likewise for dibutyl succinate: 843, 1123, 1303, 1439 and 1463 $cm^{-1}$ and for diisopropyl succinate: 833, 876, 1149, 1185, 1469 (most intense band) and 1733 $cm^{-1}$.

The Raman spectra were obtained with a spectrometer of dispersive Raman type equipped with an ionised argon laser (514 nm). The laser beam is focussed on the sample by means of a microscope equipped with a x50 long working distance objective. The power of the laser at the level of the sample is of the order of 1 mW. The Raman signal given off by the sample is collected by the same objective and is dispersed by means of an 1800 rpm network and then collected by a CCD detector. The spectral resolution obtained is of the order of 0.5 $cm^{-1}$. The recorded spectral range is between 300 and 1800 $cm^{-1}$. The acquisition period has been fixed at 120 s for each Raman spectrum recorded.

The dialkyl succinate is advantageously dimethyl succinate, dibutyl succinate or diiosopropyl succinate.

Preferably the dialkyl succinate used is dimethyl succinate and the catalyst in its spectrum has the main Raman bands at 990 and/or 974 $cm^{-1}$ characteristic of the Keggin heteropolyanion or heteropolyanions, and 853 $cm^{-1}$ characteristic of dimethyl succinate.

Preparation Process According to the Invention

More precisely the subject of the invention is a process for the preparation of a catalyst from a catalytic precursor comprising a support based on alumina and/or silica-alumina and/or zeolite and comprising at least one element of group VIB and optionally at least one element of group VIII, said process comprising impregnation of said precursor with a solution of a C1-C4 dialkyl succinate, characterised in that it comprises the following steps:
1) impregnation (step 1) of said dried, calcined or regenerated precursor with at least one solution containing at least one carboxylic acid other than acetic acid, then maturing and drying at a temperature lower than 200° C., possibly followed by a heat treatment at a temperature lower than 350° C., preferably lower than 300° C.,
2) followed by an impregnation step (step 2) with a solution containing at least one C1-C4 dialkyl succinate and then maturing and drying at a temperature lower than 200° C. without a subsequent calcination step,
and the catalytic precursor and/or the solution of step 1 and/or the solution of step 2 contains phosphorus.

Preferably the Catalytic Precursor Contains Phosphorus.

Preferably the first step (step 1) is impregnation of the dried, calcined or regenerated catalytic precursor with a solution containing a carboxylic acid, optionally acetic acid and optionally phosphorus, which are preferably diluted in a solvent. That impregnation operation is followed by a step for maturing of said impregnated catalytic precursor and then drying at a temperature lower than 200° C.

Preferably the second step (step 2) is impregnation of the catalytic precursor resulting from step 1 with a solution containing C1-C4 dialkyl succinate in the presence or not of a compound containing phosphorus and with optionally (and preferably) acetic acid, followed by a step for maturing of said catalytic precursor resulting from step 1, which is impregnated, then a drying operation at a temperature lower than 200° C. without a subsequent calcination step (heat treatment in air).

The catalyst obtained is preferably subjected to a sulphuration step to be activated prior to its use.

The catalytic precursor of step 1 (its composition and the heat treatments will be described in detail hereinafter).

The catalytic precursor comprises a support based on alumina and/or silica-alumina and/or zeolite and at least one element of group VIB, optionally at least one element of group VIII and optionally phosphorus. Said element or elements has or have been introduced preferably by impregnation of said support with at least one solution of said element or elements. Impregnation is followed by drying at a temperature lower than 200° C. and most often lower than 180° C. The result obtained is a "dried catalytic precursor".

The drying operation can be followed by a calcination operation in an oxidising atmosphere at a temperature of at least 350° C., the product will be referred to as the "calcined catalytic precursor". The calcination temperature is lower than 600° C. and most often lower than 550° C.

The catalytic precursor can be a regenerated catalyst. It has been used for example in hydrotreatment and/or hydroconversion processes. The catalyst after use is said to be "spent" and its deactivation is such that regeneration is needed. A catalyst which has been regenerated will be referred to as the "regenerated catalytic precursor".

Regeneration permits combustion of the carbon deposited on the catalyst upon its industrial use. It can be implemented by all the means known to the man skilled in the art. Regeneration is generally performed at temperatures of between 350 and 550° C. and most often between 400 and 520° C. or between 420 and 520° C. or again between 450 and 520° C., while temperatures lower than 500° C. are often advantageous.

The process for preparation of a catalyst according to the invention comprises the following preparation steps:
1) at least one impregnation step using a solution comprising at least one carboxylic acid which preferably is citric acid, optionally at least one phosphorus compound and optionally acetic acid,
followed by a maturing step and a drying operation at a temperature lower than 200° C., followed possibly by a heat treatment at a temperature lower than 350° C. Preferably drying is effected at 100-180° C.
2) then at least one impregnation step using an impregnation solution comprising at least one C1-C4 dialkyl succinate, optionally at least one phosphorus compound, in particular if phosphorus has not been introduced by impregnation in its totality previously, and optionally (and preferably) acetic acid,
followed by a maturing step and a drying step at a temperature lower than 200° C. without subsequent calcination step. Preferably drying is effected at 50-160° C.

Preferably the product obtained at the end of step 2) is subjected to a sulphuration step. The invention also concerns the sulphurated catalyst.

It is possible to envisage other embodiments which are still embraced by the invention, for example after the drying operation in step 1, the catalytic precursor is subjected to a heat treatment above the initial drying temperature and below the calcination temperature (which is often at least 350° C.), preferably the temperature of the treatment being lower than 300° C. That embodiment makes it possible in particular to envisage the use of heavy carboxylic acid (high boiling point).

These quick simple preparation processes with unitary steps do not exceed some hours and thus permit better productivity on an industrial scale than the processes in the prior art.

As will be described hereinafter the process according to the invention is preferably performed with the following modes taken alone or in combination:
the catalytic precursor contains all of the hydrogenating function (that is to say the totality of the elements of group GVIB and, if they are present, the totality of the elements of group VIII), which was preferably introduced by impregnation upon preparation of the fresh catalytic precursor, upon preparation of the fresh catalyst all of the phosphorus is introduced into the catalytic precursor, the impregnation solutions of steps 1 and 2 do not contain any phosphorus, the dialkyl succinate is dimethyl succinate, the carboxylic acid is citric acid, steps 1) and/or 2) are carried out in the presence of water and/or ethanol and in particular step 1), step 2) is performed in the presence of acetic acid, the maturing steps are performed at a temperature between 17 and 60° C., drying of the impregnated product of step 1 is performed at a temperature between 100 and 180° C., and drying of the impregnated product of step 2 is performed at a temperature between 50 and 160° C.

The Catalytic Precursor

The dried or calcined catalytic precursor of the preparation process according to the invention or having resulted in the regenerated catalytic precursor can be prepared by all the methods well known to the man skilled in the art.

The Support

The support of the catalytic precursor is based on alumina and/or silica-alumina and/or zeolite.

Preferably it contains solely alumina and/or silica-alumina and/or zeolite with optionally the metal or metals and/or dopant or dopants which were introduced outside of the impregnation operations (introduced for example upon preparation—mixing, peptisation . . . of the support or shaping thereof). The support may contain one or more dopants such as boron, phosphorus or fluorine. The support may also contain any other element known to the man skilled in the art, which can be introduced into the support outside of the impregnation operations.

In an embodiment the support generally contains more than 10%, indeed 25%, indeed more than 35% and preferably more than 50% by weight of alumina. Preferably the support is formed by alumina. Preferably the alumina is gamma alumina and preferably said support is formed by gamma alumina.

In another embodiment the support is a silica-alumina containing preferably at most 1%, indeed 10%, indeed at most 25%, preferably at most 35% and still more preferably at least (or more than) 50% of alumina. The content of silica in the support is at most 99% by weight, indeed less than 90%, preferably less than or equal to 65% by weight and more preferably less than or equal to 50% by weight. Preferably the support is formed by silica-alumina.

In another embodiment the support of the catalytic precursor contains one or more zeolites in addition to the alumina and/or silica-alumina, in a proportion generally less than 50% by weight, preferably less than 45% by weight and very preferably less than 40% by weight.

The zeolite or the mixture of zeolites contained in the support of the catalytic precursor used according to the invention comprises at least one series of channels, the opening to which is defined by a ring containing 12 oxygen atoms (12 MR). That zeolite is selected from the zeolites defined in the classification "Atlas of Zeolite Structure Types", Ch. Baerlocher, L. B. Mc Cusker, D. H. Olson, 6th Edition, Elsevier, 2007, Elsevier" having at least one series of channels whose pore opening is defined by a ring containing 12 oxygen atoms. The initially used zeolite before being modified advantageously contains in addition at least one series of channels whose pore opening is defined by a ring containing 12 oxygen atoms (12 MR) at least one series of channels whose pore opening is defined by a ring containing 8 oxygen atoms (8 MR) and/or at least one series of channels whose pore opening is defined by a ring containing 10 oxygen atoms (10 MR). Preferably the zeolites of structural type FAU and BEA which are or are not modified are used. They are mixed with the alumina and/or silica-alumina in the operation of shaping the support. Preferably the zeolite or zeolites used have been modified to permit the creation of mesoporosity by desalumination and/or desilication or by any other methods known to the man skilled in the art.

The support formed by alumina and/or silica-alumina and/or zeolite can be shaped by any procedure known to the man skilled in the art. The shaping operation can be performed for example by extrusion, by pelleting, by the drop coagulation (oil drop) method, by granulation on a rotating plate or by any other method well known to the man skilled in the art.

The Hydrogenating Function

The catalytic precursor contains a hydro-dehydrogenating function. It is performed by at least one element of group VIB and optionally by at least one element of group VIII and preferably at least one element of group VIII and at least one element of group VIB.

The total content of hydro-dehydrogenating elements is advantageously greater than 6% by weight of oxygen with respect to the total weight of the catalyst. The preferred elements of group VIB are molybdenum and tungsten and in particular molybdenum. The preferred elements of group VIII are non-noble elements and in particular cobalt and nickel. Advantageously the hydro-dehydrogenating function comprises (and is preferably formed by) molybdenum, nickel and/or cobalt.

Advantageously the hydrogenating function is selected from the group formed by the combinations of the elements cobalt-molybdenum, nickel-molybdenum or nickel-cobalt-molybdenum or nickel-molybdenum-tungsten.

In the case where considerable activity in terms of hydrodesulphuration or hydrodenitrification and hydrogenation of aromatics is desired the hydro-dehydrogenating function is advantageously implemented by the association of nickel and molybdenum; an association of nickel and tungsten in the presence of molybdenum may also be advantageous. In the case of charges of the type of distillates under vacuum or heavier distillates, combinations of cobalt-nickel-molybdenum type may advantageously be used.

The precursors of those elements and in particular molybdenum and tungsten of group VIII which can be used are also well known to the man skilled in the art, as well as their manner of introduction. Reference will be made for example to patent application WO2011/80407.

The amount of precursor or precursors of the element or elements of group VIB is advantageously between 5 and 40% by weight of oxides of group VIB with respect to the weight of the dried, calcined or regenerated catalytic precursor, in other words a deduced loss on ignition (at 550° C., atmospheric pressure), of preferably between 8 and 35% by weight and very preferably between 10 and 30% by weight.

The amount of precursor or precursors of the element or elements of group VIII is advantageously between 1 and 10% by weight of oxides of group VIII with respect to the weight of the dried, calcined or regenerated catalytic precursor, in other words a deduced loss on ignition preferably between 1.5 and 9% by weight and very preferably between 2 and 8% by weight.

The Dopants

Phosphorus is always present in the catalyst obtained. It was generally introduced upon impregnation of the support with one at least of the elements of the hydro-dehydrogenating function and it is therefore present on the catalytic precursor. It can also be introduced upon impregnation with the carboxylic acid or acids in step 1) of the process and/or upon impregnation with the succinate (step 2) of the process.

In the case where the process according to the invention is used for preparing fresh dried or calcined catalyst the phosphorus is preferably introduced in its totality on the catalytic precursor, preferably by impregnation.

Another dopant can also be present which is preferably selected from boron and fluorine taken alone or as a mixture. The dopant is an added element which in itself does not have any catalytic character but which increases the catalytic activity of the metal or metals.

The sources of boron or fluorine are known as well as their manner of introduction and reference will be made for example to patent application WO2011/80407.

The preferred phosphorus source is orthophosphoric acid $H_3PO_4$, but its salts and esters like ammonium phosphates are also suitable. The phosphorus can also be introduced at the same time as the element or elements of group VIB in the form of Keggin, lacunary Keggin, substituted Keggin or Strandberg type heteropolyanions.

The dopant is introduced into the catalytic precursor in an amount of oxide of said dopant with respect to the weight of catalyst, deduced loss on ignition (at 550° C., atmospheric pressure):

- between 0 and 40% by weight preferably between 0 and 30% by weight and still more preferably between 0 and 20% by weight, preferably between 0 and 15% by weight and still more preferably between 0 and 10% by weight when said dopant is boron; when boron is present, the minimum amount is preferably 0.1% or preferably 0.5% by weight,
- between 0.1 (or 0.5%) and 20% by weight, preferably between 0.1 (or 0.5%) and 15% by weight and still more preferably between 0.1 (or 0.5%) and 10% by weight when said dopant is phosphorus, and
- between 0 and 20% by weight, preferably between 0 and 15% by weight and still more preferably between 0 and 10% by weight when said dopant is fluorine; when fluorine is present the minimum amount is preferably 0.1% or 0.5% by weight.

Advantageously the phosphorus is introduced in its totality or in respect of part thereof in the form of a mixture with the precursor or precursors of the hydro-dehydrogenating function on the shaped amorphous support, preferably extrudates of alumina or silica-alumina by dry impregnation of said amorphous support by means of a solution containing the precursor salts of the metals and the precursor or precursors of the dopant or dopants.

Still more preferably the "catalytic precursor" of the process according to the invention and in particular the fresh dried or calcined precursor is prepared with an impregnation solution containing at least one precursor of each element of the hydro-dehydrogenating function in the presence of a phosphorus precursor, the support being formed by alumina and/or silica-alumina and/or zeolite.

It is possible to add an additive to enhance catalytic activity. For example the fresh (non-spent) catalytic precursor can also have been prepared in accordance with the preparation process described in WO2011/80407. It is also possible to envisage replacing the succinate/acid pair by the succinate alone or by any other organic compound known for enhancing activity of the catalyst; those compounds are known; they are for example C1-C10 alcohols comprising at least 2 alcohol functions, carboxylic acid alone such as citric acid, complexing molecules . . . . Those precursors will be referred to as "additive-bearing catalytic precursors". In general they are treated in accordance with the process of the present invention after having been spent and regenerated (that is to say in the state of a regenerated precursor).

The Heat Treatments to which the Catalytic Precursor can be Subjected

The dried catalytic precursor was obtained by drying at a temperature lower than 200° C. and most often lower than 180° C. It is for example between 50 and 180° C., preferably between 60 and 150° C. or again between 65 and 145° C. and very preferably between 70 and 140° C. or again between 75 and 130° C.

The dried catalytic precursor was optionally calcined at a temperature of at least 350° C. The calcination temperature is lower than 600° C., and most often lower than 550° C., for example from 350 to 550° C., and preferably between 400 and 520° C. or preferably between 420 and 520° C. or between 450 and 520° C., temperatures lower than 500° C. are often advantageous.

In another mode the spent catalyst is regenerated. Regeneration is a heat treatment in the presence of oxygen, pure or diluted. The aim of this step is to eliminate at least a part of the coke present on the catalyst due to combustion. There is no chemical treatment in this step.

The regeneration treatment can be performed at a temperature between 350 et 550° C. and generally between 450 et 520° C. or between 420 and 520° C. or between 400 et 520° C. It is preferably performed at between 420 and 500° C. or between 450 and 520° C. according to the nature of the carbon to be burnt. The man skilled in the art will optimise the temperature necessary for burning the coke (or its precursors), while avoiding or minimising fritting of the catalyst.

During that step monitoring of the temperature is necessary so as to permit combustion of the coke but not exceed 550° C. on the catalyst, including locally. Exceeding the temperature of 550° C. could for example result in damaging its porosity. That monitoring operation is known to the man skilled in the art. The temperature within the bed during that regeneration phase can be monitored by any procedure known to the man skilled in the art, such as for example arranging thermocouples in the mass of the catalyst.

When this step is performed with a mixture comprising oxygen the diluent can be selected from nitrogen or any other inert gas. The oxygen content can be fixed all through the treatment or can vary in the course of the regeneration process. For example the temperature may vary in the course of the treatment in a number of phases, the temperatures can vary from the ambient temperature to the final coke combustion temperature, which is always lower than 550° C. The duration of that regeneration step will depend on the amount of catalyst to be treated and the nature and amount of coke present.

That duration can vary in practice from 0.1 hour to a few days. In most cases it is between 1 hour and 20 hours.

Steps 1 and 2

Step 1)

In accordance with step 1) of the process according to the invention the dried or calcined or regenerated catalytic precursor is impregnated with an impregnation solution comprising at least one carboxylic acid, optionally at least one phosphorus compound and optionally acetic acid.

Those compounds are advantageously introduced into the impregnation solution of step 1) of the process according to the invention in an amount (with respect to the catalytic precursor) corresponding to:
- a molar ratio of carboxylic acid per element or elements of group VIB of the catalytic precursor of between 0.05 and 5.0 mole/mole, preferably between 0.1 and 4.0 mole/mole, preferably between 0.2 and 3.0 mole/mole and very preferably between 0.5 and 2.0 mole/mole,
- a molar ratio of phosphorus per element or elements of group VIB of the catalytic precursor of between 0 and 1.0 mole/mole, preferably between 0 and 0.8 mole/mole, preferably between 0 and 0.6 mole/mole and very preferably between 0 and 0.5 mole/mole,
- and, when acetic acid is present, a molar ratio of acetic acid per element or elements of group VIB of the catalytic precursor of between 0.1 and 6.0 mole/mole, preferably between 0.5 and 5.0 mole/mole, preferably between 1.0 and 4.0 mole/mole and very preferably between 1.5 and 2.5 mole/mole,
- the molar ratio of carboxylic acid+acetic acid per element or elements of group VIB of the catalytic precursor being between 0.15 and 11.0 mole/mole.

Said impregnation solution can advantageously be deposited in one or more steps either by impregnation in slurry form, or by impregnation in excess, or by dry impregnation, or by any other means known to the man skilled in the art. Preferably it is a single dry impregnation step.

The impregnation solution comprises at least one carboxylic acid other than acetic acid, optionally at least one phosphorus compound and optionally acetic acid. Preferably the carboxylic acid is citric acid.

The impregnation solution may contain a polar solvent. It is advantageously selected from the group formed by methanol, ethanol, water, phenol and cyclohexanol alone or as a mixture. It can also be selected from the group formed by propylene carbonate, DMSO (dimethyl sulphoxide) or sulpholane alone or as a mixture. Preferably a protic polar solvent is used. A list of the usual polar solvents and their dielectric constant can be found in the book "Solvents and Solvent Effects in Organic Chemistry", C. Reichardt, Wiley-VCH, 3rd edition, 2003, pages 472-474.

Preferably the solvent is water and/or ethanol and preferably the impregnation solution is an aqueous solution.

The carboxylic acids which can be used in the present invention contain 1 to 20 carbon atoms with at least one COOH function and preferably at least 2 COOH functions. It is possible to use acids having up to 3, 4 and indeed up to 6 COOH functions. Those acids may also contain other heteroatoms (sulphur and nitrogen) and the chemical functions associated therewith. A preferred embodiment involves using carboxylic acids not containing any other heteroatoms. Such acids can then be selected from the following non-exhaustive list: formic acid, maleic acid, propionic acid, butyric acid, valeric acid, caproic acid, enanthic acid, caprylic acid, pelargonic acid, capric acid, undecylic acid, lauric acid, tridecylic acid, benzoic acid, salicylic acid, malonic acid, succinic acid, glutaric acid, adipic acid, pimelic acid, suberic acid, azelaic acid, phthalic acid, isophthalic acid, glycolic acid, lactic acid, malic acid, tartric acid and citric acid. The acids comprising two carboxylic functions or more will be preferred. In particular citric, tartric, malic, malonic, glutaric and succinic acid are preferred. Citric acid is still more preferred.

Preferably the impregnation solution contains solely citric acid and optionally acetic acid as well as water and/or ethanol. Preferably it is an aqueous solution of citric acid.

The impregnation solution may contain a non-protic solvent known to the man skilled in the art, in particular toluene or xylene.

The man skilled in the art will select the solvent or solvents in dependence on compatibility with the components of the solution.

The maturing conditions are described hereinafter.

The catalytic precursor impregnated in that way is subjected to a drying step. The aim of that step is to remove all or part of the possible solvent having permitted introduction of the carboxylic acid, this being before step 2).

That drying step is advantageously effected by any procedure known to the man skilled in the art. It is advantageously performed at atmospheric pressure or at reduced pressure. Preferably this step is performed at atmospheric pressure.

It is performed at a temperature lower than 200° C., generally between 50 and 200° C., preferably between 60 and 190° C. Very preferably it is lower than 180° C., preferably between 60 and 180° C., and advantageously between 80 and 180° C. or 100 and 180° C. Generally operation is implemented in those temperature ranges and without subsequent heat treatment at a temperature of 200° C. or more.

It is advantageously performed in a tunnel furnace, in a fluidised bed, in a vibrated fluidised bed, in a fluidised bed with exchangers, in a cross-flow bed or with any technology permitting drying. Preferably the gas used is either air or an inert gas like argon or nitrogen. Very preferably drying is effected in nitrogen.

Preferably the duration of that step is between 30 minutes and 4 hours and preferably between 45 minutes and 3 hours.

The drying operation permits removal of a part or all of the solvent, which liberates the porous volume and makes it available for step 2. Preferably the drying temperature is higher than the boiling or decomposition temperature of the carboxylic acid. This makes it possible to eliminate all or part of the acid. In certain cases and in particular where a heavy acid is used, as described hereinbefore, it may be advantageous to prolong the drying operation by a heat treatment at a temperature lower than 350° C.

Step 2)

The dried or calcined or regenerated catalytic precursor which has been impregnated and dried or subjected to heat treatment in accordance with step 1) is now impregnated with an impregnation solution comprising at least one C1-C4 dialkyl succinate (and in particular dimethyl succinate) and optionally at least one phosphorus compound and possibly acetic acid.

Those compounds are advantageously introduced into the impregnation solution in an amount (with respect to the catalytic precursor) corresponding to:
- a molar ratio of dialkyl succinate (for example dimethyl succinate) per element or elements of group VIB of the catalytic precursor of between 0.1 and 2.0 mole/mole, preferably between 0.2 and 1.8 mole/mole, preferably between 0.2 and 1.5 mole/mole and very preferably between 0.5 and 1.0 mole/mole,
- a molar ratio of phosphorus per element or elements of group VIB of the catalytic precursor of between 0 and 1.0 mole/mole, preferably between 0 and 0.8 mole/mole, preferably between 0 and 0.6 mole/mole and very preferably between 0 and 0.5 mole/mole,
- and, when acetic acid is present, a molar ratio of acetic acid per element or elements of group VIB of the catalytic precursor of between 0.1 and 6 mole/mole, preferably between 0.3 and 5 mole/mole, preferably between 0.5 and 3 mole/mole and very preferably between 0.7 and 2.0 mole/mole.

Said impregnation solution can advantageously be deposited in one or more steps either by impregnation in slurry form, or by impregnation in excess, or by dry impregnation, or by any other means known to the man skilled in the art. Preferably it is a single dry impregnation step.

A preferred impregnation solution comprises at least one dialkyl succinate and at least one phosphorus compound and optionally acetic acid. Another preferred impregnation solution comprises at least dialkyl succinate, acetic acid and optionally at least one phosphorus compound. Preferably the solution contains acetic acid. Preferably the solution contains dimethyl succinate and acetic acid.

The impregnation solution may contain a polar solvent. It is advantageously selected from the group formed by methanol, ethanol, water, phenol and cyclohexanol alone or as a mixture. It can also be selected from the group formed by propylene carbonate, DMSO (dimethyl sulphoxide) or sulpholane alone or as a mixture. Preferably a protic polar solvent is used. A list of the usual polar solvents and their dielectric constant can be found in the book "Solvents and Solvent Effects in Organic Chemistry", C. Reichardt, Wiley-VCH, 3rd edition, 2003, pages 472-474.

Preferably the solvent is water and/or ethanol and preferably the impregnation solution is an aqueous solution.

The dialkyl succinate used is preferably included in the group formed by dimethyl succinate, diethyl succinate, dipropyl succinate, diisopropyl succinate and dibutyl succinate. Preferably the C1-C4 dialkyl succinate used is dimethyl succinate or diethyl succinate. Very preferably the C1-C4 dialkyl succinate used is dimethyl succinate. At least one C1-C4 dialkyl succinate is used, preferably one alone, and preferably dimethyl succinate.

The Maturing Conditions

The maturing operation is a step in which the impregnated solution is left in contact with the catalytic precursor. Maturing in the two steps is advantageously effected at atmospheric pressure. The temperature is generally between 17° C. and 60° C. or more advantageously between 17° C. et 50° C. Generally the maturing duration is greater than 10 minutes, preferably between 10 minutes and 48 hours, still more preferably between 20 minutes and 24 hours and advantageously between 30 minutes and 6 hours. A duration of 6 hours of often sufficient. Longer durations however are not to be ruled out.

A simple way of adjusting the maturing duration in step 2) is to characterise the formation of Keggin heteropolyanions by Raman spectroscopy. Very preferably, to enhance productivity without altering the amount of heteropolyanions reformed the duration of the maturing operation at ambient temperature is between 30 minutes and 6 hours. That duration can be reduced on condition of heating the impregnated precursor to a temperature of at most 60° C.

In the same way a way of adjusting the duration of the first maturing step is to characterise the disappearance of the crystalline species which are refractory, in respect of sulphuration, for example $CoMoO_4$. That can be done by DRx or in a still finer fashion by Raman spectroscopy (doublet of lines at 939 and 948 $cm^{-1}$).

Final Drying

The product which is impregnated in that way in accordance with step 2) is subjected to a drying step. The aim of this step is to obtain a transportable, storable and handleable catalyst, in particular for loading the hydrotreatment unit. This involves removing all or part of the possible solvent having permitted introduction of the C1-C4 dialkyl succinates (in particular dimethyl succinate). In all cases this involves imparting a dry aspect to the catalyst in order to avoid the extrudates sticking to each other during the transport, storage, handling or loading steps.

This drying step is advantageously effected by any procedure known to the man skilled in the art. It is advantageously effected at atmospheric pressure or at reduced pressure. Preferably this step is performed at atmospheric pressure.

It is performed at a temperature lower than 200° C., generally between 50° C. and 200° C., preferably between 60 and 190° C. Very preferably it is lower than 180° C. preferably between 50° C. (or 60° C.) and 180° C. (or 160° C.), and advantageously between 80 and 180° C. or 50 and 160° C. Operation is effected without a subsequent heat treatment at a temperature of 200° C. or more.

It is advantageously performed in a tunnel furnace, in a fluidised bed, in a vibrated fluidised bed, in a fluidised bed with exchangers, in a cross-flow bed or with any technology permitting drying. Preferably the gas used is either air or an inert gas like argon or nitrogen. Very preferably drying is effected in nitrogen.

Preferably the duration of that step is between 30 minutes and 4 hours and preferably between 45 minutes and 3 hours.

At the end of step 2) after the process according to the invention the result obtained is a dried catalyst which is not subjected to any subsequent calcination step or subsequent thermal treatment at a temperature of 200° C. or more.

The catalyst obtained at the end of step 2) has a Raman spectrum comprising the most intense bands at 990 and/or 974 $cm^{-1}$ (heteropolyanions of Keggin type), the bands corresponding to the succinate (for dimethyl succinate the most intense band is at 853 $cm^{-1}$).

Sulphuration

Before its use it is advantageous to transform the catalyst obtained at the end of step 2) into a sulphurated catalyst in order to form its active phase. That activation or sulphuration phase is effected by methods known to the man skilled in the art and advantageously in a sulpho-reducing atmosphere in the presence of hydrogen and hydrogen sulphide.

At the end of step 2) the dried catalyst obtained is therefore advantageously subjected to a sulphuration step without intermediate calcination step. A sulphurated catalyst according to the invention is the result.

The dried catalyst is advantageously sulphurated in ex situ or in situ fashion. The sulphurating agents are the gas $H_2S$ or any other compound containing sulphur used for activation of hydrocarbon charges for sulphurating the catalyst. The sulphur-bearing compounds are advantageously selected from alkyl disulphides such as for example dimethyl disulphide (DMDS), alkyl sulphides such as for example dimethy sulphide, n-butylmercaptan, polysulphide compounds of tertiononyl polysulphide type such as for example TPS-37 or TPS-54 marketed by ARKEMA, or any other compound known to the man skilled in the art which makes it possible to achieve good sulphuration of the catalyst. Preferably the catalyst is sulphurated in situ in the presence of a sulphurating agent and a hydrocarbon charge. Very preferably the catalyst is sulphurated in situ in the presence of a hydrocarbon charge with the addition of dimethyl disulphide.

Hydrotreatment and/or Hydroconversion Process Using the Catalyst Obtained at the End of Step 2 and Preferably Activated:

Finally another subject of the invention is a process for hydrotreatment of hydrocarbon charges using the catalyst prepared according to the invention. Such processes are for example processes for hydrodesulphuration, hydrodenitrification, hydrodemetalation and hydrogenation of aromatics, which processes will be included in the name "hydrotreatment". Another subject of the invention is a process for hydroconversion of hydrocarbon charges using the catalyst prepared according to the invention.

The dried catalysts obtained by the process of the invention and preferably having been previously subjected to a sulphuration operation are advantageously used for the reactions for the hydrotreatment of hydrocarbon charges such as petroleum cuts, the cuts resulting from the conversion of coal or hydrocarbons produced from natural gas. Those catalysts are for example advantageously used in the pre-treatment of catalytic cracking charges or hydrodesulphuration of residues or advanced hydrodesulphuration of diesels (ULSD Ultra Low Sulphur Diesel).

The catalysts obtained by the process according to the invention and having preferably been previously subjected to a sulphuration step have improved activity relative to the catalysts in the prior art.

The charges used in the hydrotreatment processes are for example petrols, diesels, vacuum diesels, atmospheric residues, vacuum residues, atmospheric distillates, vacuum distillates, heavy fuels, oils, waxes and paraffins, used oils, residues or crudes which have been deasphalted, charges resulting from thermal or catalytic conversion processes, taken alone or as mixtures. The charges which are treated and in particular those set out hereinbefore generally contain heteroatoms such as sulphur, oxygen and nitrogen and, as regards the heavy charges, they most often also contain metals.

The operating conditions used in the processes involving reactions for the hydrotreatment of hydrocarbon charges as described hereinbefore are generally as follows: the temperature is advantageously between 180 and 450° C., and preferably between 250 and 440° C., the pressure is advantageously between 0.5 and 30 MPa, and preferably between 1 et 18 MPa, the hourly space velocity is advantageously between 0.1 and 20 h$^{-1}$ and preferably between 0.2 and 5 h$^{-1}$, and the hydrogen/charge ratio expressed in terms of volume of hydrogen, measured under normal temperature and pressure conditions, per volume of liquid charge is advantageously between 50 L/L and 2000 L/L.

The hydroconversion process operates in the presence of hydrogen at a temperature higher than 200° C., preferably between 250 and 480° C., preferably between 320 and 450° C., very preferably between 330 and 435° C., under a pressure higher than 1 MPa, preferably between 2 and 25 MPa, preferably between 3 and 20 MPa, at a space velocity of between 0.1 and 20 h$^{-1}$, preferably between 0.1 and 6 h$^{-1}$, preferably between 0.2 and 3", and the amount of hydrogen introduced is such that the ratio by volume of litre of hydrogen/litre of hydrocarbon is between 80 and 5000 L/L and most often between 100 and 3000 L/L. Those operating conditions generally make it possible to achieve conversion rates per pass, in respect of products having boiling points lower than 300° C. and better lower than 340° C., and even better lower than 370° C., of at least 50% by weight and still more preferably between 20 and 100% but most generally between 60 and 95% by weight.

Highly different charges can be treated by the processes according to the invention as described hereinbefore. They advantageously contain at least 20% by volume and preferably at least 80% by volume of compounds boiling above 340° C.

The charge is advantageously selected from LCO (Light Cycle Oils: light oils resulting from a catalytic cracking unit), atmospheric distillates, vacuum distillates such as for example resulting from direct distillation of the crude or conversion units such as the FCC, coker or viscoreduction, charges from units for extraction of aromatics of lubricating oil bases or from deparaffining with a solvent of lubricating oil bases, distillates from processes for desulphuration or hydroconversion in a fixed bed, in a boiling bed or in a slurry of ATR (atmospheric residues) and/or VR (vacuum residues) and/or deasphalted oils and the deasphalted oils alone or as a mixture. The foregoing list is not limitative.

BRIEF DESCRIPTION OF THE DRAWING

FIG. 1 represents Raman spectra of materials in accordance with the invention.

EXAMPLES

The following examples demonstrate the considerable gain in activity on the catalysts prepared with the process according to the invention in relation to the catalysts in the prior art and set forth the invention more precisely without however limiting the scope thereof.

Example 1

Preparation of the Catalysts A1, A2 and A3 (not According) and A4 (According)

A matrix composed of ultrafine tabular boehmite or alumina gel marketed by Condéa Chemie GmbH was used. That gel was mixed with an aqueous solution containing 66% nitric acid (7% by weight of acid per gram of dry gel) then worked for 15 minutes. At the end of that working operation the paste obtained is passed through a die having cylindrical orifices of a diameter equal to 1.6 mm. The extrudates are then dried for one night at 120° C. and then calcined at 600° C. for 2 hours in moist air containing 50 g of water per kg of dry air. That gives support extrudates solely composed of cubic gamma alumina of low crystallinity.

Cobalt, molybdenum and phosphorus are added to the above-described alumina support which is in the extruded form. The impregnation solution is prepared by hot dissolution of molybdenum oxide (24.34 g) and cobalt hydroxide (5.34 g) in the solution of phosphoric acid (7.74 g) in aqueous solution. After dry impregnation the extrudates are left to mature at ambient temperature (20° C.) in a water-saturated atmosphere for a period of 12 hours and then they are dried for one night at 90° C. The dried catalytic precursor A1 is obtained. A fraction of the dried catalyst is then calcined at 450° C. for 2 hours. The calcined catalyst A2 is obtained. The final composition of the catalysts A1 and A2 expressed in the form of oxides is then as follows: $MoO_3$=22.5±0.2 (% by weight), CoO=4.1±0.1 (% by weight) and $P_2O_5$=4.0±0.1 (% by weight).

The catalyst A3 is prepared by dry impregnation of the dried precursor A1 with a solution comprising dimethyl succinate and acetic acid which are diluted in water. The intended contents of dimethyl succinate (DMSU) and acetic acid (AA) are respectively 27% by weight and 18% by weight (that is to say AA/Mo=1.9 mol/mol and DMSU/Mo=1.2 mol/mol). After a maturing period of 3 hours in a closed vessel at ambient temperature the catalyst is again dried in a flow of nitrogen (1 NL/g/g) for a period of 1 hour in a cross-flow bed at 140° C.

The catalyst A4 is prepared by dry impregnation of the calcined precursor A2 with a solution of citric acid diluted in water. The intended contents of citric acid (CA) are 10% by weight (that is to say CA/Mo=0.35 mol/mol). After a maturing period of 12 hours in a closed vessel at ambient temperature the catalyst is dried in a flow of nitrogen (1 NL/g/g) for a period of 2 hours in a furnace of the cross-flow bed type at 180° C. The catalyst is then impregnated dry with a solution comprising dimethyl succinate and acetic acid which are diluted in water. The intended contents of dimethyl succinate (DMSU) and acetic acid (AA) are respectively 18% by weight and 17% by weight (that is to say AA/Mo=1.8 mol/mol and DMSU/Mo=0.8 mol/mol). After a maturing period of 3 hours in a closed vessel at ambient temperature the catalyst is again dried in a flow of nitrogen (1 NL/g/g) for a period of 1 hour in a cross-flow bed at 140° C.

Example 2

Preparation of the Regenerated Catalyst B31

The catalyst A3 is loaded into a cross-flow bed unit and sulphurated by a direct distillation diesel with the addition of 2% by weight of dimethyl disulphide. An HDS test on a mixture of direct distillation diesel and a diesel from catalytic cracking is then implemented for 600 hours. After the test the spent catalyst is discharged, collected and washed with toluene under reflux for 12 hours and then separated into two batches. The first batch is regenerated in a controlled combustion furnace while introducing for each temperature stage increasing amounts of oxygen, which makes it possible to limit the exothermy linked to combustion of the coke. The final regeneration stage is at 480° C. The catalyst regenerated in that way is analysed by DRX. The presence of a line at 26° characteristic of the presence of crystallised $CoMoO_4$ is noted. In addition this catalyst which hereinafter will be referred to as B31 is of a very pronounced bright blue colour.

Example 3

Preparation of the Catalysts C31 and C31bis (not According) from the Regenerated Precursor B31—Implementation with Citric Acid Alone The catalysts C31 and C31 bis are prepared by dry impregnation of the regenerated catalyst B31 with a solution of citric acid diluted in water. The intended contents of citric acid (CA) are 10% by weight (CA/Mo=0.35 mol/mol). After a maturing period of 12 hours in a closed vessel at ambient temperature the catalyst is divided into 2 batches: the first is dried in a flow of nitrogen (1 NL/g/g) for a period of 2 hours in a furnace of cross-flow bed type at 180° C., resulting in the catalyst C31. The second batch is dried in identical fashion but with a reference temperature of 140° C., resulting in the catalyst C31bis.

Example 4

Preparation of a Catalyst D31 and D31bis (According) from the Regenerated Precursor—Implementation with DMSU The catalyst D31 is prepared by dry impregnation of the regenerated catalyst C31 with a solution comprising pure dimethyl succinate (DMSU). That amounts to aiming at 32% by weight of dimethyl succinate on the final catalyst (that is to say DMSU/Mo=1.4 mol/mol). After a maturing time of 3 hours in a closed vessel at ambient temperature the catalyst is again dried in a flow of nitrogen (1 NL/g/g) for a period of 1 hour in a cross-flow bed at 140° C.

The catalyst D31bis is prepared by dry impregnation of the regenerated catalyst C31 with a solution comprising pure dimethyl succinate (DMSU). That amounts to aiming at 30% by weight of dimethyl succinate on the final catalyst (that is to say DMSU/Mo=1.3 mol/mol). After a maturing time of 3 hours in a closed vessel at ambient temperature the catalyst is again dried in a flow of nitrogen (1 NL/g/g) for a period of 1 hour in a cross-flow bed at 140° C.

The catalysts D31 and D31bis were analysed by Raman spectroscopy. They both have in particular the main band of Keggin HPA at 990 $cm^{-1}$.

Example 5

Preparation of a Regenerated Catalyst E31 and E31bis (According)—Implementation with DMSU and Acetic Acid The catalyst E31 is prepared by dry impregnation of the regenerated catalyst C31 with a solution comprising dimethyl succinate and acetic acid which are diluted in water. The intended contents of dimethyl succinate (DMSU) and acetic acid (AA) are respectively 18% by weight and 17% by weight (that is to say AA/Mo=1.8 mol/mol and DMSU/Mo=0.8 mol/mol). After a maturing period of 3 hours in a closed vessel at ambient temperature the catalyst is again dried in a flow of nitrogen (1 NL/g/g) for a period of 1 hour in a cross-flow bed at 140° C.

The catalyst E31bis is prepared by dry impregnation of the regenerated catalyst C31 bis with the same solution as for E31, comprising dimethyl succinate and acetic acid which are diluted in water. The intended contents of dimethyl succinate (DMSU) and acetic acid (AA) are respectively 17% by weight and 17% by weight (that is to say AA/Mo=1.8 mol/mol and DMSU/Mo=0.7 mol/mol). After a maturing period of 3 hours in a closed vessel at ambient temperature the catalyst is again dried in a flow of nitrogen (1 NL/g/g) for a period of 1 hour in a cross-flow bed at 140° C.

The catalysts E31 and E31bis were analysed by Raman spectroscopy. They have in particular the main band of the Keggin HPA at 990 $cm^{-1}$, but also a shoulder at 850 $cm^{-1}$ characteristic of dimethyl succinate (FIG. 1).

Example 6

Preparation of a Regenerated Catalyst F31 (not According)—Implementation in One Step The catalyst F31 is prepared by dry impregnation of the regenerated catalyst B31 with a solution comprising dimethyl succinate, citric acid and acetic acid which are diluted in water. The intended contents of citric acid (CA), dimethyl succinate (DMSU) and acetic acid (AA) are respectively 10% by weight, 18% by weight and 17% by weight (that is to say CA/Mo=0.3 mol/mol, DMSU/Mo=0.8 mol/mol and AA/Mo=1.8 mol/mol). After a maturing period of 12 hours in a closed vessel at ambient temperature the catalyst is again dried in a flow of nitrogen (1 NL/g/g) for a period of 2 hours in a cross-flow bed at 160° C.

Example 7

Comparative Test of Catalysts A1, A2, A3, A4, B31, C31, C31bis, D31, D31bis, E31, E31 bis, F31 in Hydrogenation of Toluene in Cyclohexane Under Pressure and in the Presence of Hydrogen Sulphide

The above-described catalysts are sulphurated in situ in a dynamic process in a tubular reactor with a fixed cross-flow bed of a pilot unit of Microcat type (manufacturer: Vinci), the fluids circulating in a downward direction. The hydrogenating activity measurements are made immediately after sulphuration under pressure and without decompression air venting with the hydrocarbons charge which served to sulphurate the catalysts.

The sulphuration and test charge is composed of 5.8% of dimethyl disulphide (DMDS), 20% of toluene and 74.2% of cyclohexane (by weight).

Sulphuration is effected from ambient temperature to 350° C. with a temperature ramp of 2° C./min, an HSV=4 h$^{-1}$ and H$_2$/HC=450 NL/L. The catalytic test is effected at 350° C. at an HSV=2 h$^{-1}$ and H$_2$/HC equivalent to that of the sulphuration process, with a minimum sampling of 4 compositions which are analysed by gaseous phase chromatography.

This therefore provides for measuring the stabilised catalytic activities of equal volumes of catalysts in the toluene hydrogenation reaction.

The detailed operating conditions under which the activity measurements are implemented are as follows:

Total pressure: 6.0 MPa
Toluene pressure: 0.37 MPa
Cyclohexane pressure: 1.42 MPa
Methane pressure: 0.22 MPa
Hydrogen pressure: 3.68 MPa
H$_2$S pressure: 0.22 MPa
Catalyst volume: 4 cm$^3$ (extrudates of a length of between 2 and 4 mm)
Hour space velocity: 2 h$^-$
Sulphuration and test temperature: 350° C.

Samples of the liquid effluent are analysed by gaseous phase chromatography. Determining the molar concentrations of unconverted toluene (T) and the concentrations in respect of its hydrogenation products (methyl cyclohexane (MCC6), ethyl cyclopentane (EtCC5) and dimethyl cyclopentanes (DMCC5)) make it possible to calculate a toluene hydrogenation rate X$_{HYD}$ defined by:

$$X_{HYD}(\%) = 100 \times \frac{MCC6 + EtCC5 + DMCC5}{T + MCC6 + EtCC5 + DMCC5}$$

The toluene hydrogenation reaction being of an order 1 under the test conditions used and the reactor behaving like an ideal plug flow reactor, the hydrogenating activity A$_{HYD}$ of the catalysts is calculated by applying the formula:

$$A_{HYD} = \ln\left(\frac{100}{100 - X_{HYD}}\right)$$

Table 1 compares the relative hydrogenating activities, that is to say which are equal to the ratio of the activity of the catalyst to the activity of the catalyst B2 (not according) taken as a reference (activity 100%) for all the catalysts prepared here.

The results of the tests are set out in Table 1.

Table 1 shows that the additivated catalysts D31 and E31 (according to the invention) prepared by the addition respectively of 32% by weight of dimethyl succinate (DMSU) and 18% by weight of dimethyl succinate (DMSU) plus 10% by weight of acetic acid to the catalyst C31 itself prepared by the addition of 10% by weight of citric acid (CA) to the catalyst B1 enjoy improved activity in relation to the starting catalyst of 52 and 62% respectively.

In comparative terms the catalysts which are not according to the invention C31 (CA alone) or F31 (simultaneous impregnation of CA, DMSU and AA) have respective gains in activity of 38 and 40%.

A reduction in the heat treatment temperature after the citric acid impregnation step leads to catalysts D31bis and E31bis (according to the invention) with levels of activity similar to or slightly less than D31 and E31 respectively. Those catalysts have in particular activities greater by 10% and 17% than the catalyst F31 impregnated in a single step.

Impregnation in two steps of a carboxylic acid then a dialkyl succinate is also advantageous on a calcined precursor, as is testified by the performances of the catalyst A4.

TABLE 1

Relative hydrogenating activities with respect to the calcined catalyst A2 (not according)

| Catalyst | Type of acid | Amount of acid (% by wt with respect to the final catalyst) | Type of organic additive (step 2) | Amount of organic additive (% by wt with respect to the final catalyst) | Impregnation number (acid and/or additive) | Relative A$_{HYD}$ with respect to A2 (%) |
|---|---|---|---|---|---|---|
| A1 (dried, not according) | — | — | — | — | — | 95 |
| A2 (calcined, not according) | — | — | — | — | — | 100 |
| A3 (dried, not according) | AA | 18 | DMSU | 27 | 1 | 170 |
| A4 (calcined, according) | CA(step1) + AA(step2) | CA = 10; AA = 17 | DMSU | 18 | 2 | 167 |
| B31 regenerated (not according) | — | 0 | — | 0 | — | 110 |
| C31 (not according) | CA | 10 | — | — | 1 | 148 |
| C31bis (not according) | CA | 10 | — | — | 1 | 151 |
| D31 (according) | CA | 10 | DMSU | 32 | 2 | 162 |
| D31 bis (according) | AC | 10 | DMSU | 32 | 2 | 160 |
| E31 (according) | CA(step1) + AA(step2) | CA = 10; AA = 17 | DMSU | 18 | 2 | 172 |
| E31bis (according) | CA(step1) + AA(step2) | CA = 10; AA = 17 | DMSU | 17 | 2 | 167 |
| F31 (not according) | CA + AA | CA = 10; AA = 17 | DMSU | 18 | 1 | 150 |

Example 8

Comparative Test of the Catalysts A2, A3, B31, C31, C31bis, E31, E31bis, F31, in Respect of Diesel HDS The above-described catalysts are sulphurated in situ in a dynamic process in a tubular reactor with a fixed cross-flow bed of a pilot unit of Microcat type (manufacturer: Vinci), the fluids circulating in a downward direction. The activity measurements are made immediately after sulphuration under pressure and without decompression air venting with a direct distillation diesel.

The sulphuration charge is composed of 2% of dimethyl disulphide (DMDS) added to a direct distillation diesel. Sulphuration is effected from ambient temperature to 350° C. A 12 hour stage at 350° C. is observed for that.

The catalytic test is effected at three temperatures: chronologically 330-335-340° C. at HSV=1 h$^{-1}$ and H$_2$/HC of 450 Nl/l, with sampling of liquid compositions every 24 hours. When the sulphur contents in the compositions are stable the temperature is changed. The test lasts about 400-450 hours in total.

The sulphur in the effluents is analysed by FX. By tracing the variation in the sulphur content in the effluents in dependence on temperature it is possible to measure the relative differences in temperatures between catalysts. The choice here is to put a figure on the differences in performance in degrees Celsius at 50 ppm: noted as T$_{50}$-HDS. Table 2 compares the activities in relation to the activity of the catalyst A2 (not according) taken as a base. For a sulphur content in the effluent of 50 ppm the catalysts having a temperature lower than that of the base catalyst are more active.

The attraction of the sequential introduction of the carboxylic acids and succinates is confirmed. E31 and E31bis prepared according to the invention thus make it possible to improve the activity of the regenerated catalyst B31 by 5 and 6° C. respectively while impregnation of citric acid alone C31 (or C31bis) makes it possible to gain only 2° C. (or 3° C.) and simultaneous impregnation of the mixture DMSU, CA, AA makes it possible to gain only 3° C.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application Ser. No. 11/04.026, filed Dec. 22, 2011, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for the preparation of a catalyst from a catalytic precursor comprising a support and a hydro-dehydrogenating function, wherein the support is based on alumina and/or silica-alumina and/or zeolite and the hydro-dehydrogenating function comprises at least one element of group VIB and optionally at least one element of group VIII, wherein said catalytic precursor contains the entirety of the hydro-dehydrogenating function elements of Group VIB and the entirety of optional elements of Group VIII, wherein the catalytic precursor contains phosphorus and wherein the catalytic precursor has been dried, calcined or regenerated, said process comprising:

1) a first step of impregnating the catalytic precursor with at least one solution consisting of at least one carboxylic acid other than acetic acid, at least one solvent, optionally acetic acid and optionally phosphorus, then maturing and drying at a temperature lower than 200° C., optionally followed by a heat treatment at a temperature lower than 350° C., to obtain a first-impregnated catalytic precursor, and 2) a second and subsequent step of impregnating the first-impregnated catalytic precursor with a solution consisting of at least one C1-C4 dialkyl succinate, at least one solvent, optionally acetic acid and optionally

TABLE 2

Relative HDS activities with respect to the calcined catalyst A2 (not according)

| Catalyst | Type of acid | Amount of acid (% by wt with respect to the final catalyst) | Type of organic additive (step 2) | Amount of organic additive (% by wt with respect to the final catalyst) | Impregnation number (acid and/or additive) | T$_{50}$-HDS (° C.) |
|---|---|---|---|---|---|---|
| A2 (calcined, not according) | — | — | — | — | — | base |
| A3 (dried, not according) | AA | 18 | DMSU | 27 | 1 | base − 6 |
| B31 Regenerated (not according) | — | 0 | — | 0 | — | base − 1 |
| C31 (not according) | CA | 10 | — | — | 1 | base − 3 |
| C31bis (not according) | CA | 10 | — | — | 1 | base − 4 |
| E31 (according) | CA(step1) + AA(step2) | CA = 10; AA = 17 | DMSU | 18 | 2 | base − 7 |
| E31bis (according) | CA(step1) + AA(step2) | CA = 10; AA = 17 | DMSU | 17 | 2 | base − 6 |
| F31 (not according) | CA + AA | 10 + 17 | DMSU | 18 | 1 | base − 4 | phosphorus, and then maturing and drying at a temperature lower than 200° C.,
wherein the first and second steps are conducted separately and without a subsequent calcination step.

2. A process according to claim 1 wherein the catalytic precursor is a catalyst which has been regenerated.

3. A process according to claim 1 wherein the C1-C4 dialkyl succinate is dimethyl succinate.

4. A process according to claim 1 wherein the carboxylic acid is citric acid.

5. A process according to claim 1 wherein the first step and/or second step are performed in the presence of water and/or ethanol as the solvent.

6. A process according to claim 1 wherein the maturing in the first step and/or second step is performed, at a temperature between 17 and 60° C.

7. A process according to claim 1 wherein the drying in the first step is performed at a temperature between 100 and 180° C.

8. A process according to claim 1 wherein the drying in the second step is performed at a temperature between 50 and 160° C.

9. A process according to claim 1 further comprising a final sulfuration step after the second step.

10. A process according to claim 1, wherein the hydro-dehydrogenating function is Mo and either Ni or Co or both Ni and Co.

11. A process according to claim 1, wherein:
the hydro-dehydrogenating function is Mo and either Ni or Co or both Ni and Co;
the C1-C4 dialkyl succinate is dimethyl succinate; and
the carboxylic acid is citric acid.

12. A process according to claim 1, wherein the solution in the second step further contains acetic acid.

13. A process according to claim 1, wherein the support is based on alumina.

14. A process for the preparation of a catalyst from a catalytic precursor comprising a support and a hydro-dehydrogenating function, wherein the support is based on alumina and/or silica-alumina and/or zeolite and the hydro-dehydrogenating function comprises at least one element of group VIB and optionally at least one element of group VIII, wherein said catalytic precursor contains the entirety of the hydro-dehydrogenating function elements of Group VIB and the entirety of optional elements of Group VIII and wherein the catalytic precursor has been dried, calcined or regenerated, said process comprising:
1) a first step of impregnating the catalytic precursor with at least one solution consisting of at least one carboxylic acid other than acetic acid, at least one solvent, phosphorus and optionally acetic acid, then maturing and drying at a temperature lower than 200° C., optionally followed by a heat treatment at a temperature lower than 350° C., to obtain a first-impregnated catalytic precursor, and
2) a second and subsequent step of impregnating the first-impregnated catalytic precursor with a solution consisting of at least one C1-C4 dialkyl succinate, at least one solvent, optionally acetic acid and optionally phosphorus, and then maturing and drying at a temperature lower than 200° C.,
wherein the first and second steps are conducted separately and without a subsequent calcination step.

15. A process according to claim 14, wherein the catalytic precursor is a catalyst which has been regenerated.

16. A process according to claim 14, wherein the C1-C4 dialkyl succinate is dimethyl succinate.

17. A process according to claim 14, wherein the carboxylic acid is citric acid.

18. A process according to claim 14, wherein the first step and/or second step are performed in the presence of water and/or ethanol as the solvent.

19. A process according to claim 14, wherein the maturing in the first step and/or second step is performed, at a temperature between 17 and 60° C.

20. A process according to claim 14, wherein the drying in the first step is performed at a temperature between 100 and 180° C.

21. A process according to claim 14, wherein the drying in the second step is performed at a temperature between 50 and 160° C.

22. A process according to claim 14, further comprising a final sulfuration step after the second step.

23. A process according to claim 14, wherein the hydro-dehydrogenating function is Mo and either Ni or Co or both Ni and Co.

24. A process according to claim 14, wherein:
the hydro-dehydrogenating function is Mo and either Ni or Co or both Ni and Co;
the C1-C4 dialkyl succinate is dimethyl succinate; and
the carboxylic acid is citric acid.

25. A process according to claim 14, wherein the solution in the second step further contains acetic acid.

26. A process according to claim 14, wherein the support is based on alumina.

27. A process according to claim 14, wherein the catalytic precursor contains phosphorus.

28. A process for the preparation of a catalyst from a catalytic precursor comprising a support and a hydro-dehydrogenating function, wherein the support is based on alumina and/or silica-alumina and/or zeolite and the hydro-dehydrogenating function comprises at least one element of group VIB and optionally at least one element of group VIII, wherein said catalytic precursor contains the entirety of the hydro-dehydrogenating function elements of Group VIB and the entirety of optional elements of Group VIII and wherein the catalytic precursor has been dried, calcined or regenerated, said process comprising:
1) a first step of impregnating the catalytic precursor with at least one solution consisting of at least one carboxylic acid other than acetic acid, at least one solvent, optionally acetic acid and optionally phosphorus, and then maturing and drying at a temperature lower than 200° C., optionally followed by a heat treatment at a temperature lower than 350° C., to obtain a first-impregnated catalytic precursor, and
2) a second and subsequent step of impregnating the first-impregnated catalytic precursor with a solution consisting of at least one C1-C4 dialkyl succinate, phosphorus, at least one solvent and optionally acetic acid, and then maturing and drying at a temperature lower than 200° C.,
wherein the first and second steps are conducted separately and without a subsequent calcination step.

29. A process according to claim 28, wherein the catalytic precursor is a catalyst which has been regenerated.

30. A process according to claim 28, wherein the C1-C4 dialkyl succinate is dimethyl succinate.

31. A process according to claim 28, wherein the carboxylic acid is citric acid.

32. A process according to claim 28, wherein the first step and/or second step are performed in the presence of water and/or ethanol as the solvent.

33. A process according to claim 28, wherein the maturing in the first step and/or second step is performed, at a temperature between 17 and 60° C.

34. A process according to claim 28, wherein the drying in the first step is performed at a temperature between 100 and 180° C.

35. A process according to claim 28, wherein the drying in the second step is performed at a temperature between 50 and 160° C.

36. A process according to claim 28, further comprising a final sulfuration step after the second step.

37. A process according to claim 28, wherein the hydro-dehydrogenating function is Mo and either Ni or Co or both Ni and Co.

38. A process according to claim 28, wherein:
   the hydro-dehydrogenating function is Mo and either Ni or Co or both Ni and Co;
   the dialkyl succinate is dimethyl succinate; and
   the carboxylic acid is citric acid.

39. A process according to claim 28, wherein the solution in the second step contains acetic acid.

40. A process according to claim 28, wherein the support is based on alumina.

41. A process according to claim 28, wherein the catalytic precursor contains phosphorus.

* * * * *